(12) United States Patent
Park et al.

(10) Patent No.: US 7,297,520 B2
(45) Date of Patent: Nov. 20, 2007

(54) LARGE CIRCULAR SENSE MOLECULE ARRAY

(75) Inventors: Jong-Gu Park, Daegu (KR); Yun-Han Lee, Daegu (KR)

(73) Assignee: Welgene, Inc., Daegu (KR)

( * ) Notice: Subject to any disclaimer, the term of this patent is extended or adjusted under 35 U.S.C. 154(b) by 284 days.

(21) Appl. No.: 10/627,882

(22) Filed: Jul. 25, 2003

(65) Prior Publication Data

US 2004/0038280 A1   Feb. 26, 2004

(30) Foreign Application Priority Data

Jul. 27, 2002   (KR) .................. 10-2002-0044411

(51) Int. Cl.
*C12N 15/66* (2006.01)
(52) U.S. Cl. .................. 435/91.41; 435/6; 435/91.4
(58) Field of Classification Search .................. None
See application file for complete search history.

(56) References Cited

U.S. PATENT DOCUMENTS

| 2002/0055099 | A1 | 5/2002 | Fisher | 435/6 |
| 2002/0168645 | A1* | 11/2002 | Taylor | 435/6 |

FOREIGN PATENT DOCUMENTS

| WO | WO 99/00520 A1 | 1/1999 |
| WO | WO 01/00786 A2 | 1/2001 |

OTHER PUBLICATIONS

Swaroop et al, Nucleic Acids Res. 19 (8), 1954 (1991).*
Molecular Biology Reagents/Protocols 1992, United States Biochemical Corporation, 1991, Cleveland, Ohio, pp. 218-219.*
Drmanac et al., Sequencing by hybridization . . . , Electrophoresis, 1992, 13: 566-573.
Kainz et al., A Modified Primer Extension Procedure . . . , Analytical Biochemistry, 1989, 179: 366-370.
Drmanac and Drmanac, Processing of cDNA and Genomic Kilobase-Size Clones . . . , BioTechniques, 1994, 17(2): 328-336.

* cited by examiner

*Primary Examiner*—James Martinell
(74) *Attorney, Agent, or Firm*—JHK Law; Joseph Hyosuk Kim

(57) ABSTRACT

Large circular (LC)-sense molecules in an array is disclosed. The LC-sense molecules array is combined with cDNA hybridization to detect differences in expression profile between different cells. LC-sense molecules were purified from nonredundant clones with recombinant phagemid and arrayed onto silanized slide glasses. By hybridization of LC-sense array with Cy3 or Cy5-labelled cDNA preparations at 60° C., 29 up-regulated and 6 down-regulated genes in cancerous liver tissue were detected.

9 Claims, 7 Drawing Sheets

FIG. 4
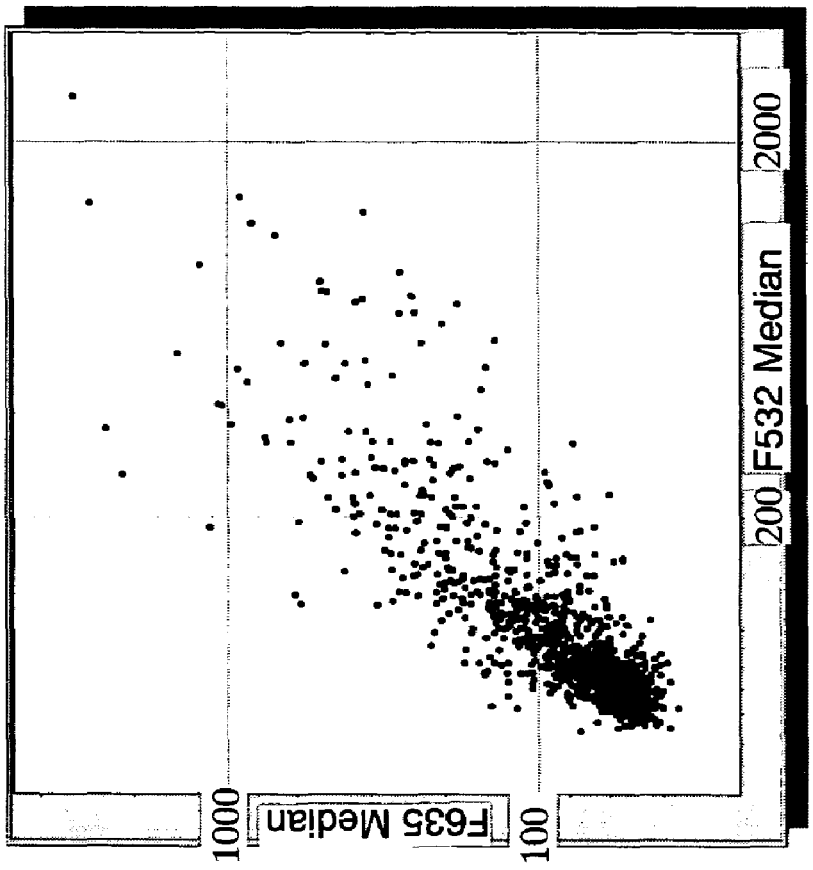
B
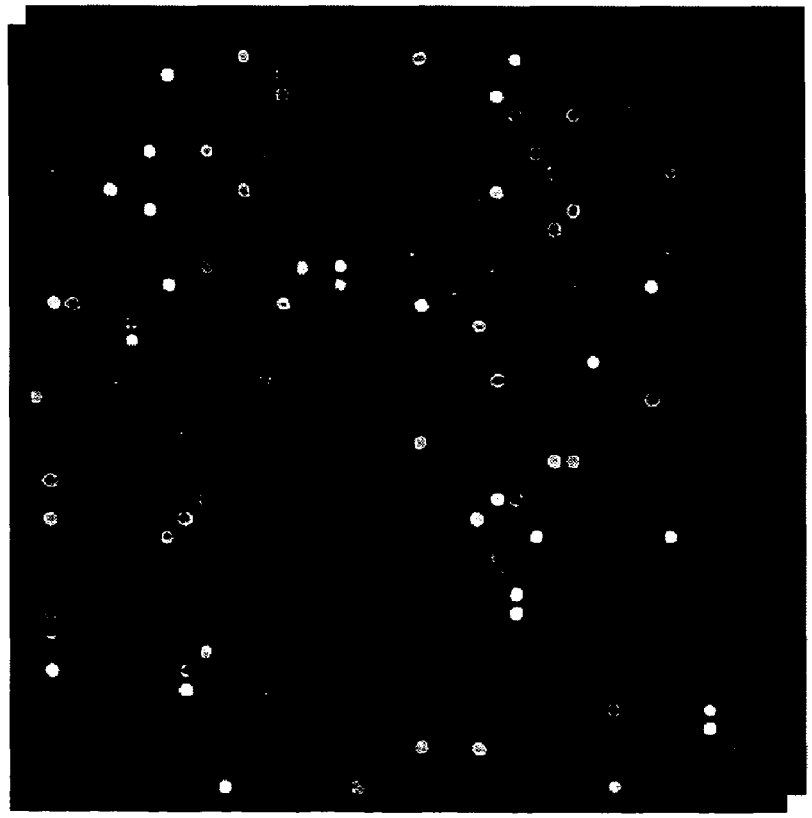
A

LARGE CIRCULAR SENSE MOLECULE ARRAY

BACKGROUND OF THE INVENTION

1. Field of the Invention

The present invention relates generally to the use of large circular (LC)-sense molecule as a probe in an array system. The invention also relates to the use of LC-sense molecule library as probes in an array system. In particular, the present invention relates to DNA chip technology, which utilizes arrays having associated single stranded LC-sense molecules. The present invention also describes methods of producing such arrays, assays for using such arrays, kits containing such arrays, and applications thereof.

2. General Background and State of the Art:

Recent developments in DNA microarray technology permits one to monitor a large number of cellular transcripts in a parallel fashion (Schena et al., *Science*, 270, 467-470 (1995), DeRisi et al., *Science*, 278, 680-686 (1997), Iyer et al., *Science*, 283, 83-87 (1999)). Both physiological and pathological changes in the function of cells are associated with alterations of gene expression patterns. For example, development of a malignancy is typically associated with both overexpression of oncogenes and decreased expression of tumor suppressor genes. Identification of differentially expressed genes has been used as a tool to recognize genes that are involved in disease process.

Various methods are available for detecting differentially expressed genes, including northern blot analysis (Alwine et al., *Proc. Natl. Acad. Sci.*, 74, 5350-5354 (1977)), S1 nuclease protection (Berk et al., *Cell*, 12, 721-732 (1977)), differential display (Liang et al., *Science*, 257, 967-971 (1992)), sequencing of cDNA libraries (Adams et al., *Science*, 252, 1651-1656 (1991), Okubo et al., *Nature Genet.*, 2, 173-179 (1992)), serial analysis of gene expression (SAGE) (Velculescu et al., *Science*, 270, 484-487 (1995)), subtractive hybridization (Hedrick et al., *Nature*, 308, 149-153 (1984)) and representational difference analysis (RDA) (Hubank et al., *Nucleic Acids Res.*, 22, 5640-5648 (1994), Lisitsyn et al., *Science*, 259, 946-951 (1993)). But these techniques are limited by the amount of data obtained from one experiment and are time-consuming to perform. Using cDNA array hybridization, the expression of thousands or tens of thousands of genes can be studied simultaneously. This has previously been done by dotting the DNA onto nylon membranes and hybridizing with radioactively labeled cDNA (Augenlicht et al., *Proc. Natl. Acad. Sci.*, 88, 3286-3289 (1991)). Recently, protocols using cDNA microarrays on glass slides, or oligonucleotides on so-called gene chips, together with fluorescent labeled probes, have been introduced (Schena et al., *Science*, 270, 467-470 (1995), Lockhart et al., *Nature Biotechnol*, 14, 1675-1680 (1996)).

Despite the wide variety of array technologies that have been developed, there is a continued need to identify new array devices to meet the needs of specific applications.

SUMMARY OF THE INVENTION

The present invention overcomes the above-mentioned problems. The present invention provides methods of preparing LC-sense molecules, a library of LC-sense molecules, and a way of fabricating LC-sense arrays, which are combined with cDNA hybridization to validate its utility for detection of differences in expression profiles between different cells. Applicants provide an array using LC-sense molecules as probing agents. Certain bacteriophages, such as M13 bacteriophage, have single stranded circular genomes, which have been conventionally employed for DNA sequencing analyses as well as mutagenesis studies. For instance, M13 phagemid, which is a plasmid used in the construction of a recombinant bacteriophage, can be engineered to produce a large quantity of circular single stranded genomic DNA that contains a target-specific sense sequence insert. This approach for producing LC-sense molecule comprising a sense DNA insert provides numerous advantages such as greater resistance to enzymatic degradation associated with its covalently closed structure, higher binding affinity for complementary nucleic acids, high sequence fidelity, elimination of laborious target site search, no requirement for modification and easy large-scale production at a low cost.

The present invention is directed to a library comprising distinct LC-sense molecules. The LC-sense molecule may comprise vector sequence and probe sequence, wherein the probe sequence is in sense orientation. The vector may be a single strand generating phagemid. Further, the LC-sense molecule may have a length of from about 1,000 to about 20,000 nucleotides. The distinct LC-sense molecules may be separated from each other or compartmentalized. In particular, the vector may be pSPORT1, pBluescriptII SK(+/−) or KS(+/−), pGEM-f, M13mp, pCR2.1, pGL2 or pβ gal. And further in particular, the vector may be M13 bacteriophage, f1 bacteriophage, or fd bacteriophage.

In another aspect, the invention is also directed to an array comprising a plurality of distinct LC-sense molecules stably associated with surface of a support. The support may comprise a coating of amino-silane, poly-L-lysine or aldehyde. Further, the support may be a slide glass, ceramic, inorganic-organic composite, flexible plastic film, silicon, metal, or membrane.

In yet another aspect of the invention, the invention is directed to a method for making the array described above, which may comprise:

(i) inserting a nucleic acid fragment into a vector that generates single stranded form of the vector;

(ii) preparing bacterial transformants by introducing the vector containing the insert into competent bacterial cells to make bacterial transformants;

(iii) infecting the transformants with helper phage to produce the LC-sense molecule;

(iv) isolating the LC-sense molecule from culture supernatant of the transformants; and (v) arraying the LC-sense molecule onto the surface of a support.

In the method described above, the nucleic acid fragment may be inserted into the vector unidirectionally for all members of the array or library.

In another embodiment, the invention is directed to a method of detecting presence of DNA in a sample with respect to a population of distinct LC-sense molecules in an array comprising:

(i) labeling the DNA in the sample;

(ii) contacting a sample containing the labeled DNA with the array described above;

(iii) allowing the labeled DNA in the sample to hybridize to the LC-sense molecule in the array; and (iv) determining binding of the DNA to the LC-sense molecule, wherein the presence of a signal on the array indicates the presence of the DNA with respect to an arrayed LC-sense molecule.

In the above-described method, the label may be streptavidin-alkaline phosphatase conjugate, chemifluorescent or chemiluminescent. In particular, the label may be Cy3 or Cy5.

In yet another embodiment, the invention is directed to a method for detecting presence of DNA in two or more samples of nucleic acid molecules, comprising:

labeling a first population of DNA from a first sample;
labeling a second population of DNA from a second sample with a different label;
contacting a sample containing the first population of labeled DNA with the array described above;
allowing the first population of labeled DNA in the sample to hybridize to the LC-sense molecule in the array;
contacting a sample containing the second population of labeled DNA with the array described above;
allowing the second population of labeled DNA in the sample to hybridize to the LC-sense molecule in the array; and
determining binding of the labeled DNA to the LC-sense molecule, wherein the presence of a signal on the array indicates the presence of the DNA.

The contacting of the at least two populations of labeled DNA to the array may occur simultaneously to the same array or the populations may be contacted in sequence to the same array or the contacting may occur on different arrays and the results compared.

In yet another embodiment of the invention, the invention is directed to a gene expression analysis kit comprising the array described above and instructions on using the array to detect DNA in a sample.

The above-described gene expression analysis kit may further comprise:

(i) a container comprising primers for generating test nucleic acids;

(ii) a container comprising dNTPs and/or rNTPs;

(iii) a container comprising post DNA synthesis labeling reagents, such as chemically active derivatives of fluorescent dyes;

(iv) a container comprising DNA synthesis enzymes;

(v) a container comprising buffer medium;

(vi) a container comprising signal generation and detection reagents; and (vii) instructions for use in detecting DNA.

The invention is further directed to a method of determining cancerous liver cell comprising detecting up regulation as compared with a normal liver cell of a gene selected from the group consisting of: Cytochrome P450, subfamily IIE (ethanol-inducible) (GenBank Accession Number J02843);

Transcription elongation factor A (SII) 1;

ESTs, Weakly similar to KIAA0206 [*H. sapiens*] (GenBank Accession Number AI193075);

Human skeletal muscle 1.3 kb mRNA for tropomyosin (GenBank Accession Number AI797037);

KIAA0701 protein (GenBank Accession Number AI797037);

mRNA for transcription elongation factor S-11, hS-II-T1 (GenBank Accession Number NM_003195);

Deafness, autosomal dominant 5 (GenBank Accession Number AF073308);

KIAA1037 protein (GenBank Accession Number AI383628);

KIAA0375 gene product (GenBank Accession Number AB002373);

Prefoldin 5 (GenBank Accession Number AA287397);

KIAA0710 gene product (GenBank Accession Number AB014610);

Paired-like homeodomain transcription factor 1 (GenBank Accession Number U70370);

Retinal outer segment membrane protein 1 (GenBank Accession Number L07894);

ESTs (GenBank Accession Number Z39419);

MYC-associated zinc finger protein (purine-binding transcription factor) (GenBank Accession Number M94046);

Ubiquitin-conjugating enzyme E2L 3 (GenBank Accession Number AJ000519);

Novel human gene mapping to chromosome 1 (GenBank Accession Number AL040438);

Homo sapiens clone 24421 mRNA sequence (GenBank Accession Number AF070641);

Homo sapiens mRNA; cDNA DKFZp566J2146 (GenBank Accession Number AL050081);

Chromosome condensation 1-like (GenBank Accession Number NM_001268);

KIAA0902 protein (GenBank Accession Number AB020709);

Protein tyrosine kinase 9-like (A6-related protein) (GenBank Accession Number AI188660);

ESTs, Weakly similar to ORF YOR150w (*S. cerevisiae*) (GenBank Accession Number AI129433);

Transcription elongation factor B (SIII), polypeptide 2 (GenBank Accession Number AW327285); and Cofactor required for Sp1 transcriptional activation, subunit 9 (GenBank Accession Number AA665998).

The invention is also directed to a method of determining cancerous liver cell comprising detecting down regulation as compared with a normal liver cell of a gene selected from the group consisting of:

Transmembrane protease, serine 2 (GenBank Accession Number U75329);

Human gene isolated from PAC 272L16, chromosome 1, similar to calcium/calmodulin dependent protein kinases (GenBank Accession Number AL023754);

CASP2 and RIPK1 domain containing adaptor with death domain (GenBank Accession Number AA811130);

Ariadne homolog (GenBank Accession Number AL040708); and

NADH dehydrogenase (ubiquinone) flavoprotein 1 (GenBank Accession Number AW250734).

These and other objects of the invention will be more fully understood from the following description of the invention, the referenced drawings attached hereto and the claims appended hereto.

BRIEF DESCRIPTION OF THE DRAWINGS

The present invention will become more fully understood from the detailed description given herein below, and the accompanying drawings which are given by way of illustration only, and thus are not limitative of the present invention, and wherein.

After purification, LC-sense molecules were run on a 1% agarose gel to test their quantity and quality. C; control LC-sense molecule without insert sequence.

Figure 3:
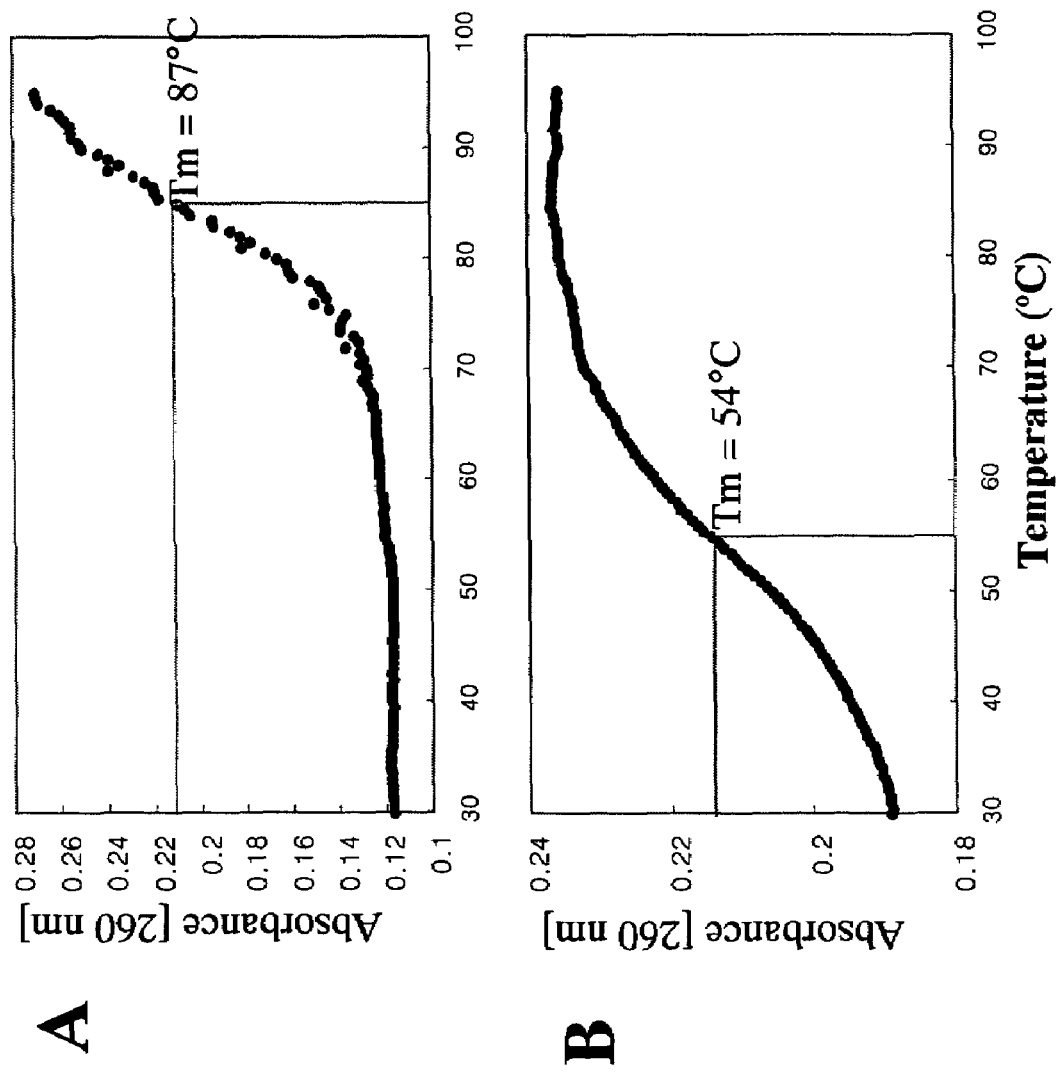

FIGS. 3A-3B show melting temperature profiles for double stranded plasmid molecules and LC-sense molecules. Absorbance was monitored at every 0.5° C. increment in a 3 min interval while temperature was raised from 30° C. to 95° C. A. Tm1/2 profile of double stranded phagemid containing the TNF-a insert. B. Tm1/2 profile of LC-sense molecules, containing the TNF-a sense insert sequence.

FIGS. 4A-4B show confirmation of RNA quality. The integrity of poly(A)+ mRNA prepared from normal and cancerous liver tissue was tested. Cy3-dUTP or Cy5-dUTP-labeled target cDNAs were mixed together and hybridized to PCR products on a cDNA chip. After hybridization, the cDNA chip was washed and scanned by scanner and analyzed by software. The data were then scatter-plotted. A: Scanned image of the cDNA chip. B: Scatter-plot for expression profile.

Figure 5:

FIG. 5 shows scanned image of a LC-sense array from cancerous liver tissue. PMT value for Cy3 and Cy5 was 450 and 500, respectively. Genes up-regulated, compared with the normal tissue, are shown in red; down-regulated genes are shown in green, and yellow represents genes showing no changes in expression.

Figure 6:
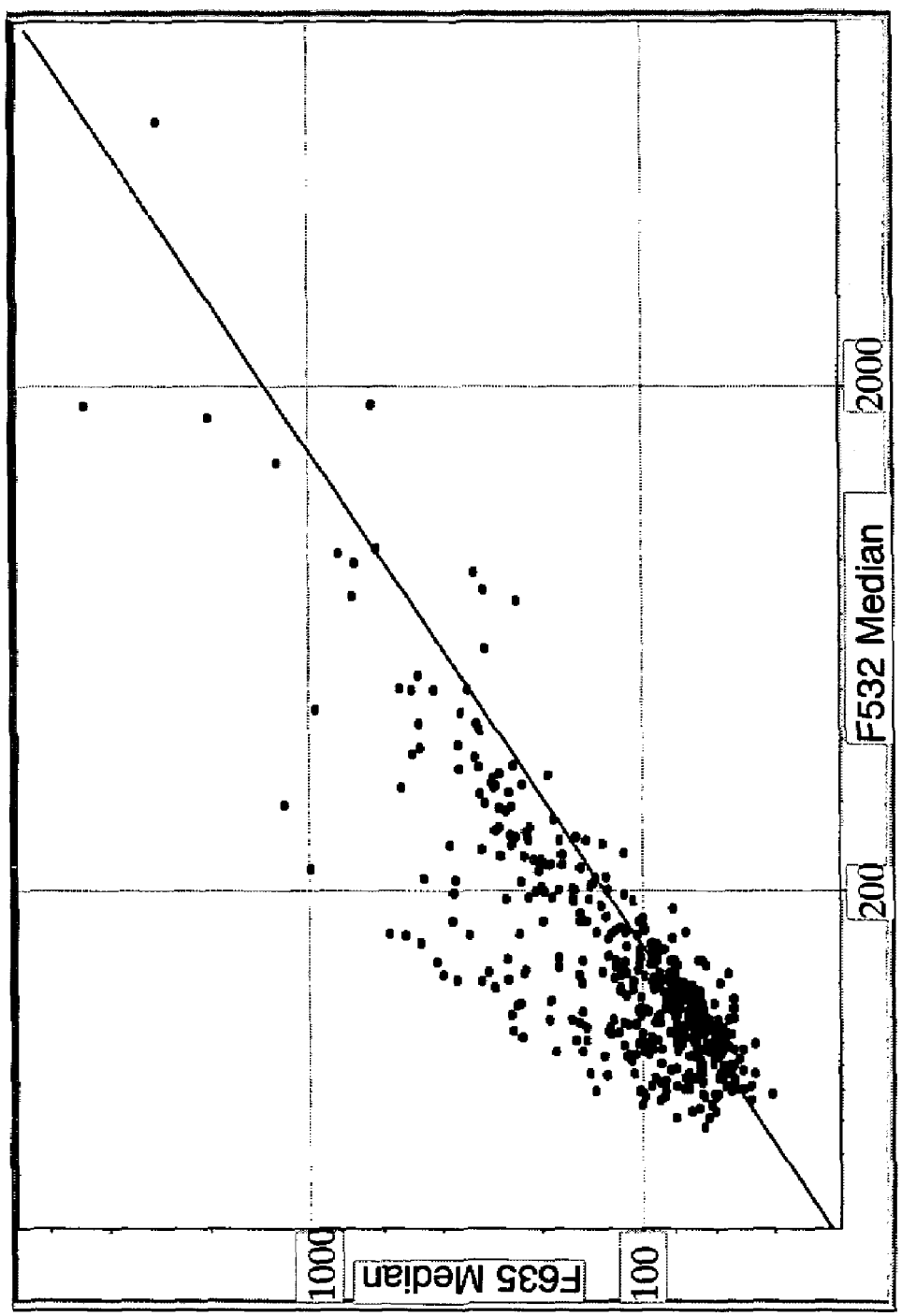

FIG. 6 shows scatter plot for expression profile comparison between normal and cancerous liver tissue. Expression profile is shown as bivariate scatter plot from a LC-sense array tested. Each spot was scatter-plotted after log2 transformation according to their intensities.

Figure 7:
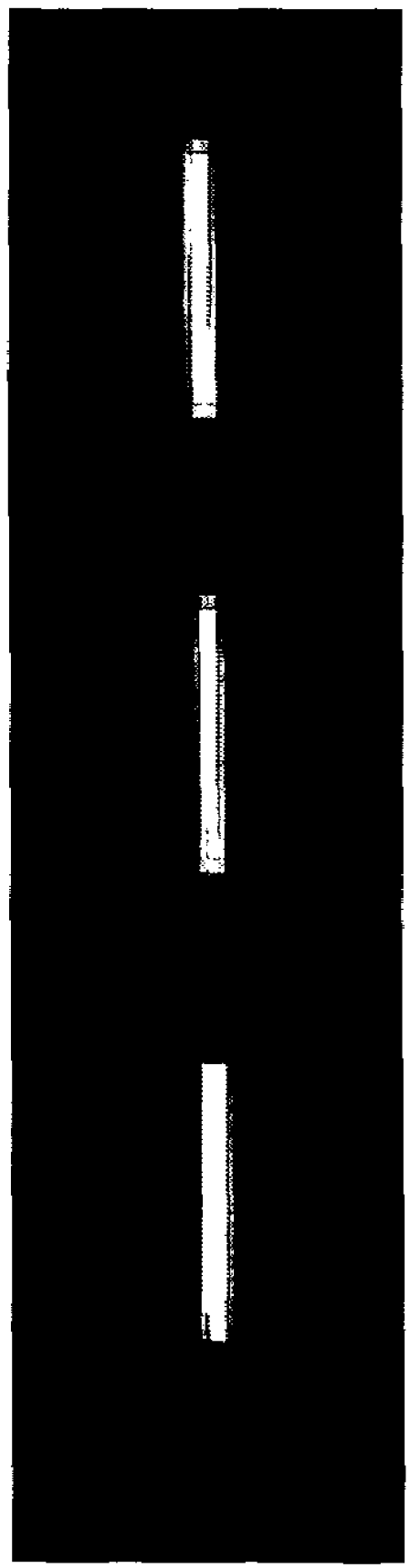

FIG. 7 shows an example of production of a LC-sense molecule in a large quantity. A transformant with a recombinant phagemid was seeded in 100 ml of 2× LB liquid media and then cultured for 14 hrs at 37° C. with constant agitation. The LC-sense molecule was obtained from 100 ml of the culture supernatant containing recombinant bacteriophages using a specially designed semi-automatic purification instrument. After preparation, LC-sense molecules were run on a 1% agarose gel and photographed under UV light for their quantitation and quantification. Lane 1, LC-sense molecule produced in a large quantity (40 ng), lane 2, LC-sense molecule produced in a large quantity (30 ng), and lane 3, LC-sense molecule produced in a small quantity (32 ng).

DETAILED DESCRIPTION OF THE PRESENT INVENTION

In the present application, "a" and "an" are used to refer to both single and a plurality of objects.

The present invention is based on the discovery that a large circular phage genomic molecule that includes a target specific sense region, is useful as an effective probe for its complementary target cDNA, in particular in an array setting. Preferably, the array is a microarray system. Preferably, the microarray system is high density in which the LC-sense molecule is spotted on a substrate plate. The inventive system can be used in a high-throughput manner in a massive array protocol to determine genes involved in various cellular physiological processes.

As used herein, an "array" or "array of regions on a solid support" refers to a linear or two-dimensional array of preferably discrete regions, each having a finite area, formed on the surface of a solid support.

As used herein, "arrayed library" refers to individual single-stranded LC-sense primary recombinant clones (hosted in the single stranded genome of phage, phagemid, or other vector) that are placed in two-dimensional arrays in microtiter (multiwell) dishes or plates. Each primary clone can be identified by the identity of the plate and the clone location (row and column) on that plate. Arrayed libraries of clones can be used for many applications, including screening for a specific gene or genomic region of interest as well as for physical mapping.

As used herein, the term "capable of hybridizing under high stringency conditions" means annealing a strand of DNA complementary to the DNA of interest under highly stringent conditions. Likewise, "capable of hybridizing under low stringency conditions" refers to annealing a strand of DNA complementary to the DNA of interest under low stringency conditions. "High stringency conditions" for the annealing process may involve, for example, high temperature and/or low salt content, which disfavor hydrogen-bonding contacts among mismatched base pairs. "Low stringency conditions" would involve lower temperature, and/or higher salt concentration than that of high stringency conditions. Such conditions allow for two DNA strands to anneal if substantial, though not near complete complementarity exists between the two strands, as is the case among DNA strands that code for the same protein but differ in sequence due to the degeneracy of the genetic code. Appropriate stringency conditions which promote DNA hybridization, for example, 6×SSC at about 45° C., followed by a wash of 2×SSC at 50° C. are known to those skilled in the art or can be found in Current Protocols in Molecular Biology, John Wiley & Sons, N.Y. (1989), 6.31-6.3.6. For example, the salt concentration in the wash step can be selected from a low stringency of about 2×SSC at 50° C. to a high stringency of about 0.2×SSC at 50° C. In addition, the temperature in the wash step can be increased from low stringency at room temperature, about 22° C., to high stringency conditions, at about 75° C. Other stringency parameters are described in Maniatis, T., et al., Molecular Cloning: A Laboratory Manual, Cold Spring Harbor Laboratory Press, Cold Spring N.Y., (1982), at pp. 387-389; see also Sambrook J. et al., Molecular Cloning: A Laboratory Manual, Second Edition, Volume 2, Cold Spring Harbor Laboratory Press, Cold Spring, N.Y. at pp. 8.46-8.47 (1989).

As used herein, "cDNA library" used with respect to the sense probe library tethered to the substrate refers to a library composed of LC-sense molecules specific to target messenger RNAs.

As used herein, "target cDNA library" used with respect to the target library refers to a collection of all of the mRNA molecules present in a cell or organism, all turned into cDNA molecules with the enzyme reverse transcriptase, so that the library can then be probed for the specific cDNA (and thus mRNA) of interest.

As used herein, "compartment" or "compartments" refers to a physical delineation of each member clone of the LC-sense molecule library. Physical delineation may be in the form of wells such as in multi-well plates. Commonly used are 96-well plates or 96-deep well plates. Another physical barrier may be air, such as by individual spotting on a flat sheet, glass or membrane. In this regard, either macroarray or microarray methods may be used. It is understood that by compartmentalization it is meant that the clone members are separated from each other. Other barriers may be by encapsulation of individual clones in a membranous material, and the like.

As used herein, a "distinct LC-sense molecule", as applied to the LC-sense molecules forming a microarray, means an array member, which is distinct from other array members on the basis of a different LC-sense DNA sequence, and/or different concentrations of the same or distinct LC-sense molecule, and/or different mixtures of distinct or different-concentration LC-sense molecule. Thus an array of "distinct LC-sense molecule" means an array containing, as its members, (i) distinct LC-sense molecule, which may have a defined amount in each member, (ii) different, graded concentrations of given-sequence LC-sense molecule, and/or (iii) different-composition mixtures of two or more distinct LC-sense molecule.

As used herein, "filamentous phage" is a vehicle for producing the LC-sense molecule of the invention. Phages or phagemids may be used. In this instance, the desired sequence is inserted or cloned into the vehicle so that when a single strand is generated by the phage or phagemid, the LC-sense molecule is generated. DNA or RNA bacteriophage may be used for this purpose. In particular, filamentous bacteriophage may be used. Filamentous phages such as M13, fd, and f1 have a filamentous capsid with a circular ssDNA molecule. Their life-cycle involves a dsDNA intermediate replicative form within the cell which is converted to a ssDNA molecule prior to encapsidation. This conversion provides a means to prepare ssDNA. The bacteriophage M13 has been adapted for use as a cloning vector.

Phagemid vectors also have filamentous phage f1 Ori region. pBluescript (Stratagene, USA), pGEM-f (Promega, USA), M13mp, pCR2.1, pGL2, pβgal and pSPORT vector and their derivatives are examples. Preferentially, a phagemid vector of M13 bacteriophage such as pBluescript SK(+/−) may be used. One advantage of using a recombinant viral vector based on M13 bacteriophage is that the vector can accommodate a variety of sizes of inserts. Because pBluescript SK(+/−) phagemid vector has f1(−/+) origin, it is possible to insert the target specific DNA fragment in a desired orientation so that the sense orientation of the inserted DNA fragment is generated.

Another useful bacteriophage having single stranded circular genome and having an icosahedral shape is FX174. However, this cloning vector has a limitation on the insert size.

As used herein, "large circular sense molecule (LC-sense molecule or LC-sense DNA)" also referred to as "phage genomic sense molecule" is a single stranded circular DNA molecule, which includes at least one sense region that is substantially complementary to and binds a target cDNA sequence, regardless of the source of the target cDNA.

The LC-sense molecule may be synthesized by a variety of methods. Typically, however, it is produced from a filamentous phage system, which includes M13 and phagemids. When the large circular nucleic acid molecule is generated from a phage, it may also be referred to as a "phage genomic sense compound".

In one aspect of the invention, the LC-sense molecule is longer than a typical oligonucleotide sequence of about 15 to 100 nucleotides. The LC-sense molecule may be at least about 3,000 nucleotides long wherein the DNA molecule may be comprised mostly of extraneous vector sequence. Typically, the range may be from about 1,000 to about 8,000 nucleotides long depending on the insert size and the size of the extraneous vector sequence. Although a length of about 3,000 to about 7,000 nucleotides may be useful in the invention, preferred length may range from about 3,300 to about 6,000 bases. It is understood that the size of the LC-sense molecule may be varied and optimized without undue experimentation so long as the LC-sense molecule selectively and specifically binds to its complementary cDNA.

Alternatively, it is understood that there does not have to be an absolute upper or lower limit to the length of the large circular nucleic acid molecule. This is especially so when a vector is used to generate the large circular nucleic acid molecule, in which case the combination of the size of the vector sequence and the size of the insert sequence that encodes at least a portion of the target gene may control the length of the single stranded nucleic acid generated. Thus, in one embodiment, the nucleic acid molecule may be as long as the vector may accommodate.

The large circular nucleic acid molecule may contain both the target specific sense sequence as well as extraneous sequence such as phage sequence. Extraneous sequence may include sense or antisense forms of various other genes. If a vector is used to generate the nucleic acid molecule, the extraneous sequence may be the vector sequence. The length of the target specific sense region of the large circular nucleic acid molecule may be without limitation from about 100 nucleotides to over about 5,000 bases. Typically, the range may be from about 200 to about 3,000. In particular, the range may be about 400 to about 2,000. In one embodiment, the target specific sense region may encode an entire gene.

In another embodiment, the LC-sense molecule may be generated from the genome of a phage or phagemid as part of its natural life cycle.

As used herein, "library" refers to an unordered collection of cloned DNA from a particular organism, whose relationship to each other can be established by physical mapping. Such a library may include more than about 10 distinct clones, and preferably may include more than 50, preferably more than 100, 200, 300, 400, 500, 600, 700, 800, 900, 1000, 1100, 1500, 2000, 2500, 3000, 4000, 5000, 7000, 10000, 15000, 20000, 25000, 30000, 35000, 40000, or 50000 distinct LC-sense molecules in a set library.

As used herein, a "microarray" refers to an array of regions having a density of discrete regions of at least about $100/cm^2$, and preferably at least about $1000/cm^2$. The regions in a microarray have typical dimensions, e.g., diameters, in the range of between about 10-250 μm, and may be separated from other regions in the array by about the same distance. The microarray may comprises a selected set of LC-sense molecules, which can be employed to examine expression of transcription or a profile of the expressed genes in a set of cells.

As used herein, "probe" used in the context of an array system is the tethered nucleic acid with known sequence. In particular, the probe is tethered to the substrate such as a glass slide.

As used herein, the term "specifically binds" refers to a non-random binding reaction between two molecules, for example between an LC-sense molecule hybridizing with its complementary sequence.

As used herein, "substantially complementary" means a nucleic acid sequence having about 80%, 85%, 90%, 96%, 97%, 98%, 99%, or 100% similarity with another nucleic acid sequence. As a general matter, absolute complementarity may not be required for specific binding to occur between two nucleic acid molecules. Any LC-sense molecule having sufficient complementarity to form a stable duplex with the target cDNA is considered to have suitable specificity of binding between the two nucleic acid molecules because stable duplex formation depends on the sequence and length of the hybridizing LC-sense molecule and the degree of complementarity between the LC-sense molecule and the target sequence.

As used herein, "target" or "targeting" in the context of an array system refers to the free nucleic acid transcript or cDNA thereof whose identity or abundance is sought to be detected by using the LC-sense probe, and in particular refers to an individual gene for which an LC-sense molecule is made. In certain contexts, "targeting" means binding or causing to be bound the LC-sense molecule to the endogenously expressed transcript or cDNA thereof. The target nucleotide sequence may be selected without limitation from any genes, and may be in particular selected from genes involved in various malignancies, including genes involved in cancer and in the initiation and progression of various diseases such as immune diseases, infectious diseases, metabolic diseases and hereditary diseases or any other disease caused by abnormal expression of genes.

As used herein, "unidirectional" or "random gene unidirectional" sense library indicates the uniformity of orientation of the insert genes in each member clone in the library. By the term "random", it is meant to refer to a library that contains genes of unverified sequence.

As used herein, "unidirectional subtracted library" refers to a library that is selectively enriched for genes that are expressed or overexpressed in a particular tissue or cell line of interest as compared with a control tissue or cell line.

As used herein, "unigene" sense library refers to a collection of sequence-verified nucleic acid fragments that are optionally inserted into a sense nucleic acid-generating vector.

Large Circular (LC) Sense Molecule

The present invention provides LC-sense compounds having enhanced stability to nucleases and specific activity, and a method for producing the LC-sense compounds by using recombinant bacteriophages with single stranded circular genome. The present invention also provides LC-sense DNA library as probe DNA for making arrays. LC-sense molecules specific to a large number of genes may be produced simultaneously in a small quantity or large quantity from a bacterial culture containing recombinant bacteriophages. In an exemplified embodiment of the invention, 1,152 different LC-sense samples were obtained in a small quantity from 3 ml of the culture supernatant and spotted onto a surface of silanized glass slide. From the 1 ml of the culture supernatant, 1~3 μg of LC-sense DNA was generally obtained.

In another exemplified embodiment of the invention, applicants designed a semi-automatic instrument which is equipped mainly with purifying columns, dispensers and a vacuum manifold for producing the LC-sense DNA library in a large quantity. Using the instrument and its ability to gather 100 ml of culture supernatant, ~200 μg of LC-sense molecules were obtained. The production scale may be enlarged up to liter units by employing a jar fermentor system for cultivation.

Further, in one embodiment of the invention, by employing the phage genomic sense method of the invention, the efficiency of the array system for high throughput detection of gene expression is superior to that of conventional methods of using oligonucleotide probes or PCR amplified larger nucleic acid probes. Thus, LC-sense molecules may be used as probes in any setting or device in which hybridization to its complementary DNA is desired.

A variety of methods are currently available for making arrays of DNA probes. LC-sense molecules may be used in such systems as probes bound to the membrane such as in arrays of nucleic acid molecules. One method for making ordered arrays of DNA on a porous membrane is a "dot blot" approach. In this method, a vacuum manifold transfers a plurality, e.g., 96, aqueous samples of DNA from 3 millimeter diameter wells to a porous membrane. A common variant of this procedure is a "slot-blot" method in which the wells have highly-elongated oval shapes. The DNA is immobilized on the porous membrane by baking the membrane or exposing it to UV radiation. This is a manual procedure practical for making one array at a time and is usually limited to 96 samples per array.

A more efficient technique employed for making ordered arrays of genomic fragments uses an array of pins dipped into the wells, e.g., the 96 wells of a microtiter plate, for transferring an array of samples to a substrate, such as a porous membrane. One array includes pins that are designed to spot a membrane in a staggered fashion, for creating an array of 9216 spots in a 22×22 $cm^2$ area.

Recently, array systems have been devised for mass fabrication of microarrays characterized by (i) a large number of micro-sized assay regions separated by a distance of 50-200 microns or less, and (ii) a well-defined amount, typically in the picomole range, of LC-sense molecules associated with each region of the array (U.S. Pat. No. 5,807,522, which is incorporated by reference herein in its entirety, especially as it relates to the microarray system).

In accordance with one aspect of the inventions, the LC-sense compounds of the present invention may be made by; 1) preparing a cDNA fragment that includes a target nucleotide sequence; 2) preparing a recombinant phage by cloning the cDNA fragment into a phagemid vector that is capable of producing a LC-sense compound; and 3) generating a single stranded circular phage genome containing the target sense sequence in a large scale manner. A library of such LC-sense molecules may be made.

Thus, in another aspect of the inventions, it is understood that the LC-sense compounds may comprise either fragments of a target sequence or the entire gene sequence. Also, it is contemplated that several target specific sense sequences for a plurality of different genes may be inserted into one single stranded phage genome. As a result, a LC-sense molecule may comprise more than one region of target specific sense sequence.

LC-sense compounds have strong replication fidelity because the compound is replicated by DNA polymerase in bacterial cells. Since DNA polymerase has proof reading capabilities, the fidelity of LC-sense compound is greater than chemically synthesized oligonucleotide. Moreover, LC-sense compounds of the present invention are cheaper to make than the chemically synthesized oligonucleotides or amplified cDNA fragments.

In another aspect of the invention, it is to be understood that each compartment in an array may comprise only LC-sense molecule. In another aspect, a compartment may contain both LC-sense molecule and its complementary counterpart such as when a double stranded phagemid is denatured to generate a LC-sense molecule strand, and its complementary single stranded counterpart. Preferably, in a region in an array the LC-sense molecule may be present in greater than a one to one ratio as compared with any complementary single stranded counterpart DNA that may be present. More preferably, the composition in a region in an array contains at least 95% LC-sense molecule. Even more preferably, the composition contains LC-sense molecule that is generated as a single stranded DNA during the life cycle of a phage which includes the insert, in which case only the single stranded LC-sense molecule may be present in the region in the array.

High-Throughput Microarray System

Large-scale expression profiling with arrays has emerged as a leading technology in the systematic analysis of cellular physiology (Young et al., Cell, 102, 9-15 (2000)). These arrays are now being applied to various applications including gene discovery (Kati et al., J. Pathol., 193, 73-79 (2001)), disease diagnosis (Alizadeh et al., Nature, 403, 503-511 (2000)), drug discovery (Leming et al., J. Chem. Inf. Comput. Sci., 40, 367-379 (2000)), toxicological research (Nuwaysir et al., Molecular Carcinogenesis, 24, 153-159 (1999)) and the like. The technology for production of microarrays utilize techniques such as building the probe oligonucleotides (usually 15-100 nucleotides) directly on the glass surface (Lipshutz et al., Biotechniques, 19, 442-447 (1995), Lipshutz et al., Nat. Genet., 21, 20-24 (1999), Singh-Gasson et al., Nat. Biotechnol., 17, 974-978 (1999)), or spotting a substrate with PCR products amplified from cDNA clone set or cDNA library (Duggan et al., Nat. Genet., 21, 10-14 (1999)). Production of arrays with oligonucleotide or PCR product has, however, some disadvantages. For example, preparation of tens of thousands of modified oligonucleotides requires sequence information, high product cost and time-consuming multiple steps, including laborious target sequence search for each gene, synthesis, desalting, column purification, concentration, modification and so on. Meanwhile, production of arrays that use PCR product requires plasmid purification, cDNA amplification with Taq polymerase, and DNA purification steps, which cost a great deal. Here, we devised an array with LC-sense molecules. Its utility as a binding agent probe for studying expression profile of genes has been demonstrated.

M13 phagemid, plasmid for the construction of a recombinant bacteriophage, is engineered to produce a large quantity of the single stranded genomic DNA that contains sense sequence because of its f1 origin. The LC-sense molecules can be produced massively from bacterial culture of competent cells with recombinant M13 phagemids by coinfection with helper bacteriophages.

In this regard, the capability of producing a large quantity of LC-sense molecules for use in array provides an advantage in lowering the cost of arrays, where conventionally the inability to easily produce large quantities of oligonucleotides and PCR produced larger cDNA products was a barrier to obtaining inexpensive array chips.

The present invention also provides a high-throughput system for functional genomics using the LC-sense molecule library discussed above. The functional genomics system of the present invention may be used to rapidly and massively search for gene function. Thus, the LC-sense library may be used for determining the interrelationships among different gene products.

Various specific array types comprising LC-sense molecules are provided by the present invention to identify differentially expressed genes in cells or tissues of diverse animals, plants, and microorganisms. These array types include, but not limited to the following: developmental array; cancer array; apoptosis array; oncogene and tumor suppressor array; cell cycle gene array; cytokine and cytokine receptor array; growth factor and growth factor receptor array; neuroarray; and so on.

The arrays of the present invention can be used in, among other applications, differential gene expression assays. For example, the arrays may be useful in the differential expression analysis of: (a) disease states, e.g., neoplastic or normal; (b) different tissue types; (c) developmental stages; (d) responses to external or internal stimulus; (e) responses to treatment; etc. The arrays may also be useful in broad scale expression screening for drug discovery and research. In addition, by studying the effect of an active agent in a particular cell type on gene expression, information for drug toxicity, carcinogenicity, environmental monitoring and the like can be obtained and analyzed.

In one aspect, the invention includes a substrate with a surface having a microarray of at least $10^3$ distinct LC-sense molecules in a surface area of less than about 1 $cm^2$. Each distinct LC-sense molecule (i) is disposed at a separate, defined position in the array, (ii) has a length of at least about 3,000 bases, and (iii) is present in a defined amount between about 0.1 femtomoles and 100 nanomoles.

In one embodiment, without being limited to any particular substrate or any particular array system, the surface may be a glass slide surface coated with a polycationic polymer, such as polylysine, and may include an array of distinct LC-sense molecules electrostatically bound non-covalently to the coating, where each distinct LC-sense molecule is disposed at a separate, defined position in a surface array.

Also forming part of the invention is a method of detecting differential expression of each of a plurality of genes in a first cell type, with respect to expression of the same genes in a second cell type. In practicing the method, there is first produced fluorescent-labeled cDNAs from mRNAs isolated from the two cell types, where the cDNAs from the first and second cell types are labeled with first and second different fluorescent reporters.

A mixture of the labeled cDNAs from the two cell types is added to an array of LC-sense molecules representing a plurality of known genes derived from the two cell types, under conditions that result in hybridization of the cDNAs to complementary-sequence LC-sense molecules in the array. The array is then examined by fluorescence under fluorescence excitation conditions in which (i) LC-sense molecules in the array that are hybridized predominantly to cDNAs derived from one of the first or second cell types give a distinct first or second fluorescence emission color, respectively, and (ii) polynucleotides in the array that are hybridized to substantially equal numbers of cDNAs derived from the first and second cell types give a distinct combined fluorescence emission color, respectively. The relative expression of known genes in the two cell types can then be determined by the observed fluorescence emission color of each spot.

A representative massive functional genomics protocol may be as follows, with the understanding that specific embodiments and exemplifications are presented without limiting the invention in any way thereby:

(1) constructing a cDNA library using a recombinant bacteriophage vector with a single stranded genome;

(2) identifying and selecting cDNA clones with insert sizes. The insert size may be at least 100, 200, 300, 400 bases, preferably at least 500 bases to at least about 2,000, 3,000, 4,000, or 5,000 bases or more. The cDNA clones may be isolated using multiple mini-scale plasmid preparation may be used;

(3) amplifying the selected clones and constructing a LC-sense library. Selected phagemid transformants are infected with helper bacteriophages. Single stranded phage genomic sense compounds are subsequently harvested from culture supernatants;

(4) dispensing distinct LC-sense molecules on a substrate such as glass, membrane, or filter in an array. The dispensing or spotting step may be carried out manually or automatically with a spotting machine.

The cells from which the target cDNA is obtained may be chosen from cells of interest such as normal cells or from cells of various types of cancer, such as liver cancer, lung cancer, stomach cancer, breast cancer, bladder cancer, rectal cancer, colon cancer, prostate cancer, thyroid cancer, and skin cancer as well as cells of obesity, hair follicles, autoimmune disorders, and metabolic disorders.

The library of LC-sense molecules may be made by randomly and unidirectionally inserting a population of cDNA inserts as in a modified shot-gun approach, or by individually identifying the sequence of an insert and cloning the insert into the phage vector so that a unique, non-redundant library of clones of interest is prepared. It is understood that the source of the random gene unidirectional LC-sense library or unigene unidirectional LC-sense library or the host cells that may be tested need not be human. According to the principles of the invention, any source organism may be used such as, but not limited to, mammals, plants, and fungi. The host cell may be also any organism, so long as the LC-sense compound is capable of penetrating the cell membrane or cell wall.

To validate the function of LC-sense molecules as binding agent for arrays, we firstly transformed recombinant pSPORT phagemid of 1,152 nonredundant clones into $E.$ $coli$ competent cell with a helper bacteriophage M13K07. The LC-sense molecules of each clone were then purified from culture supernatant and were concentrated up to 0.2~0.5 mg/ml on a large scale. With this method, we obtained 1,152 samples. As array substrates for binding agent, poly-L-lysine or amino-silane were coated on the surface of glass to enhance the immobilization of the nucleic acids (Schena et al., $Proc.$ $Natl.$ $Acad.$ $Sci.$ $USA$, 93, 10614-19 (1996)). After confirming the quality and quantity of LC-sense molecules by agarose gel electrophoresis, LC-sense arrays were prepared by spotting those molecules on silanized slide glasses using a microarrayer. After confirming the quality of poly(A+) RNA purified from normal and cancerous liver tissue, labelled cDNA probes were mixed and hybridized to LC-sense arrays comprising 1,152 non-redundant samples.

RNA obtained from normal liver cells and cancerous liver tissue are reverse transcribed into cDNA in the presence of nucleotides labeled with radiolabelled or fluorescent tags. Cy3-dNTP and Cy5-dNTP dyes are the most commonly used fluorophores, as labeling agents. The incubation of the target with the conventional microarray comprising oligonucleotides or amplified cDNA product has been typically performed at 45° C. or 65° C., respectively, for aqueous hybridization buffers. However, we optimized hybridization temperature at 60° C. based on the determination of melting temperature of single stranded LC-molecules. These distinctions of optimal temperature for hybridization reflect the structural difference between LC-sense molecule probes and conventionally used oligonucleotides or PCR products. Following hybridization, the LC-sense array was washed repeatedly to remove the unbound and non-specific signal. Scanning analysis by software showed that 29 of 1,152 genes were up-regulated and 6 genes were down-regulated in cancerous liver tissue as compared with normal tissue. With these results, we confirmed that LC-sense molecules work well as a probe on slide glass arrays.

LC-sense array provides several advantages for use in an array system used for studying expression profile of genes. First, LC-sense molecules can be produced on a large scale with speed, accuracy and cost effectiveness from bacterial transformants, such as $E.$ $coli$. Second, the phagemid vector can accommodate a variety of sizes of sense inserts. Due to its long sequence, binding specificity can be remarkably enhanced. Third, making an array with LC-sense molecules does not require the time consuming act of searching for target binding sequence. Fourth, LC-sense molecules have strong replication fidelity because the molecule is replicated by DNA polymerase in bacterial cells. Since DNA polymerase has proof reading capabilities, the fidelity of LC-sense molecule is greater than chemically synthesized oligonucleotides or cDNA that is amplified in a tube. Fifth, LC-sense molecules are cheaper to make than the chemically synthesized oligonucleotides or amplified PCR products. Finally, due to utilization of vector-based techniques, construction of a LC-sense molecule library with a large number of individual clones may be performed easily and rapidly. A library specific to a particular disease can be easily constructed from diseased cells or abnormal cells or tissue. From these libraries, we can easily produce LC-sense molecules on a large scale and discover a panel of disease-related genes, which may include those genes of unknown functions. Otherwise, from a library constructed with little or no redundancy among its members of the entire panel of human genes or genes of other organisms, diverse expression profile of various diseases can be achieved as described herein. In an additional step, for more efficient discovery of an anticancer drug, a combination of suppression subtractive hybridization (SSH) and cDNA array hybridization methods may be used (Kati et al., J. Pathol., 193, 73-79 (2001)). By utilizing phagemid vectors with f1 origin for the construction of the subtracted cDNA library, the process of making a unidirectional library of random genes overexpressed in a particular cell or tissue is made easier. Gene expression profile obtained from LC-sense arrays has been confirmed with further methods including real time PCR and northern blotting.

In one general embodiment, the surface is a relatively hydrophilic, i.e., wettable surface, such as a surface having native, bound or covalently attached charged groups. One such surface described below is a glass surface having an absorbed layer of a polycationic polymer, such as poly-L-lysine.

In another embodiment, the surface has or is formed to have a relatively hydrophobic character, i.e., one that causes aqueous medium deposited on the surface to bead. A variety of known hydrophobic polymers, such as polystyrene, polypropylene, or polyethylene have desired hydrophobic properties, as do glass and a variety of lubricant or other hydrophobic films that may be applied to the support surface.

The slide may be coated by placing a uniform-thickness film of a polycationic polymer, e.g., poly-L-lysine, on the surface of a slide and drying the film to form a dried coating. The amount of polycationic polymer added may be sufficient to form at least a monolayer of polymers on the glass surface. The polymer film may be bound to the surface via electrostatic binding between negative silyl-OH groups on the surface and charged amine groups in the polymers. Poly-L-lysine coated glass slides may be obtained commercially, e.g., from Sigma Chemical Co. (St. Louis, Mo.).

To form the microarray, defined volumes of distinct LC-sense molecules are deposited on the polymer-coated slide. According to an important feature of the substrate, the deposited LC-sense molecules remain bound to the coated slide surface non-covalently when an aqueous DNA sample is applied to the substrate under conditions which allow hybridization of reporter-labeled cDNA in the sample to the LC-sense DNA probe in the substrate array.

In a preferred embodiment, each microarray contains at least $10^3$ distinct LC-sense molecules per surface area of less than about 1 cm$^2$. The microarray may contain at least about 400 regions in an area of about 16 mm$^2$, or $2.5 \times 10^3$ regions/cm$^2$. Also in a preferred embodiment, the LC-sense molecules in each microarray region may be present in a defined amount between about 0.1 femtomoles and 100 nanomoles in the case of polynucleotides.

Also in a preferred embodiment, the polynucleotides have lengths of at least about 3000 bp, i.e., substantially longer than oligonucleotides which can be formed in high-density arrays by various in situ synthesis schemes.

Labels

Suitable enzyme labels include, for example, those from the oxidase group, which catalyze the production of hydrogen peroxide by reacting with substrate. Glucose oxidase is particularly preferred as it has good stability and its substrate (glucose) is readily available. Activity of an oxidase label may be assayed by measuring the concentration of hydrogen peroxide formed by the enzyme-labeled antibody/substrate reaction. Besides enzymes, other suitable labels include radioisotopes, such as iodine ($^{125}$I,$^{121}$I), carbon ($^{14}$C), sulphur ($^{35}$S), tritium ($^{3}$H), indium ($^{112}$In), and technetium ($^{99m}$Tc), and fluorescent labels, such as fluorescein and rhodamine, and biotin.

Examples of suitable radioisotopic labels include $^{3}$H, $^{111}$In, $^{125}$I, $^{131}$I, $^{32}$P, $^{35}$S, $^{14}$C, $^{51}$Cr, $^{57}$To, $^{58}$Co, $^{59}$Fe, $^{75}$Se, $^{152}$Eu, $^{90}$Y, $^{67}$Cu, $^{217}$Ci, $^{211}$At, $^{212}$Pb, $^{47}$Sc, $^{109}$Pd, etc. Examples of suitable non-radioactive isotopic labels include $^{157}$Gd, $^{55}$Mn, $^{162}$Dy, $52^{Tr}$, and $^{56}$Fe.

Examples of suitable fluorescent labels include an $^{152}$Eu label, a fluorescein label, an isothiocyanate label, a rhodamine label, a phycoerythrin label, a phycocyanin label, an allophycocyanin label, an o-phthaldehyde label, a fluorescamine label, cyanine (Cy3™), and indocarbocyanine (Cy5™).

Examples of chemiluminescent labels include a luminal label, an isoluminal label, an aromatic acridinium ester label, an imidazole label, an acridinium salt label, an oxalate ester label, a luciferin label, a luciferase label, and an aequorin label.

Examples of nuclear magnetic resonance contrasting agents include heavy metal nuclei such as Gd, Mn, and iron. Deuterium may also be used. Other contrasting agents also exist for EPR, PET or other imaging mechanisms, which are known to persons of skill in the art.

Kit

The invention also includes a kit for analyzing samples for the presence of cDNA in a sample. In a general embodiment, the kit comprises a substrate on which is an array of LC-sense molecules in one or more containers. In a specific embodiment, the kit of the present invention may contain reagents, NTPs, enzymes, columns, and test nucleic acids specifically reacting with an array. Preferably, the kit of the present invention may further comprise nucleic acids which do or do not react with the microarray. The kit further comprises instructions and labels on its use.

The present invention is not to be limited in scope by the specific embodiments described herein. Indeed, various modifications of the invention in addition to those described herein will become apparent to those skilled in the art from the foregoing description and accompanying figures. Such modifications are intended to fall within the scope of the appended claims. The following examples are offered by way of illustration of the present invention, and not by way of limitation.

EXAMPLES

Example 1

LC-Sense Array

Recombinant pSPORT1 phagemids were transformed into bacterial competent cells (XL-10 Gold, Stratagene, USA) that had been infected with a helper bacteriophage M13K07 (NEB Nucleic Acids, USA) and incubated on LB agar plate containing ampicillin (50 µg/ml) for overnight at 37° C. Well-isolated transformants were seeded in each well of 96-deep well plate containing 1.4 ml of 2×YT liquid media (tryptone 16 g, yeast extract 10 g, NaCl 10 g/1000 ml) containing 50 µg/ml of ampicillin and 70 µg/ml of kanamycin and cultured for 14 hrs at 37° C. with vigorous shaking. This incubation was carried out in triplicate for each clone to maximize the yield of LC-sense molecules in a single purification. For production of LC-sense molecules in a small quantity, 3 ml of culture supernatant was added with 1/5 volume of 20% polyethylene glycol (PEG 8000) and 2.5M NaCl, and was transferred onto QIAprep 96 M13 Kit (Qiagen, German). Purification steps were performed with QIAVAC Vacuum Manifold (Qiagen, German) according to manufacturer's instructions. LC-sense molecules prepared were run on a 1% agarose gel to test their quantity and quality. The eluates were then dried and redissolved in 10 µl of 3×SSC to adjust concentration of LC-sense molecules and were arrayed onto the surface of a silanized glass slide (CMT-GAPS, Corning, USA) using an OmniGrid Microarrayer (GeneMachines, Inc., USA). Each slide was crosslinked with 300 mJ irradiation of short-wave UV (Stratalinker, Stratagene, USA) and stored in a desiccator until use.

Example 2

Production of LC-Sense Molecules of Rat TNF-α

Rat TNF-α cDNA was cloned into the multiple cloning site of the phagemid vector, pBluescript (pBS)-KS(+). Production of recombinant M13 phage was carried out by infecting M13K07 helper phages into bacterial cells that were already transformed with pBS KS (+) phagemid. F1 replication origin of the phagemid was utilized to generate LC-sense molecules for the target gene. Twenty percent polyethylene glycol (PEG 8000) was added to the supernatant of an overnight culture of cells infected with helper phages. The bacteriophage precipitate was resuspended in TE (pH 8.0), and phage genomic DNA was isolated by phenol extraction and ethanol precipitation. Purification of LC-sense molecules from the residual genomic DNA of helper bacteriophage and host bacterial cells was carried out either with 0.8% low melting point (LMP) agarose gel for small scale purification or with gel filtration column chromatography (1.0×50 cm) for large scale purification. The column resin for gel filtration was superfine Sephacryl™ S-1000 (molecular cutoff: 20,000 bp) (Amersham Pharmacia Biotech AB, Sweden), and was packaged and equilibrated with 50 mM Tris-HCl buffer containing 0.2 M NaCl (pH 8.3). The starting volume of the LC-molecules was adjusted to 5% of the gel void volume and DNA elution was carried out with the same buffer used for resin equilibration (flow rate: 0.3 ml/min). Samples were UV scanned at 260/280 nm with a dual UV detection system and were collected every 5 min during elution. Sample fractions were washed and precipitated with 70% cold ethanol and were resuspended in distilled ultra-pure water and PBS (phosphate-buffered saline) for subsequent experiments. The purified LC-molecules were tested for quantity and purity on a 1% agarose gel.

Example 3

$T_m$ Assay

Thermal denaturation of the single stranded LC-molecules of rat TNF-a and double stranded plasmid DNA (pBS]-KS(+) phagemid containing the TNF-a insert was performed in a solution of 100 mM NaCl, 10 mM $MgCl_2$ and 10 mM sodium PIPES (Sigma, USA). DNA at 10 µg/ml (10 nM) was heated to 95° C. and allowed to cool slowly to room temperature prior to denaturation experiments. The temperature was raised at a rate of 0.5° C./3 min. Melting studies were carried out in a diode array spectrophotometer equipped with a Peltier temperature controller (Hewlett Packard, USA).

Example 4

RNA Preparation

Total RNA preparation of normal and cancerous liver tissue was carried out with Tri reagent (MRC, USA) according to the protocol recommended by the manufacturer. Tissues were washed with phosphate-buffered saline and sliced into smaller pieces. Sliced tissues were then homogenized for 10 min in an optimal volume of Tri Reagent. Purification of poly(A)$^+$ mRNA was done with a poly (A) Quick mRNA Isolation Kit (Stratagene, USA) according to manufacturer's instructions. Purified poly(A)$^+$ mRNA was used as template for preparation of target DNAs.

Example 5

Target cDNA Preparation and Hybridization

The overall procedure for hybridization was performed according to Dr. Patrick O. Brown's lab protocol (http://cmgm.stanford.edu/pbrown). Briefly, 2 µg each of poly(A)$_+$ mRNA from liver normal and tumor tissue was reverse-transcribed using oligo-dT primers in the presence of Cy3-dUTP or Cy5-dUTP, respectively. The labeled cDNA was then purified through a microcon-30 column. The purified target cDNA was resuspended in 80 µl of hybridization solution (3×SSC and 0.3% SDS) and then denatured at 100° C. for 2 min and applied to an array of LC-sense molecules. Hybridization was carried out at 60° C. for 16 hr in a humidified chamber. Finally, the hybridized slide was washed once each in 2×SSC for 2 min, 0.1×SSC, 0.1% SDS for 5 min, and 0.1×SSC for 5 min and then spun-dried prior to scanning at room temperature.

Example 6

Data Acquisition and Analysis

Fluorescent target cDNAs hybridized to a cDNA microarray were detected by scanning the slide with a GenePix 4000B scanner (Axon instruments, USA). The PMT (photomultiplier tubes) value for Cy3 or Cy5 was 450 and 500, respectively. The scanned image was then analyzed using the GenePix Pro 3.0 software package. Signal intensity values were determined by subtracting the background median value from the intensity median value of each spot. Expression values were normalized by a single multiplicative normalization factor and applied to all Cy5/Cy3 ratios so that the median normalized Cy5/Cy3 ratio became 1.0.

Example 7

Preparation of LC-Sense Molecules in a Large Quantity

A recombinant phagemid was transformed into competent E. coli cells that had been infected with helper bacteriophages, M13K07. The transformed cells were incubated on an LB agar plate containing ampicillin (50 µg/ml) for overnight at 37° C. A single colony was carefully isolated and seeded in 100 ml of LB liquid media (bactotryptone 10 g, yeast extract 5 g, NaCl 10 g/1000 ml, 50 µg/ml of ampicillin, and 70 µg/ml of kanamycin). Cells were then cultured for 14 hrs at 37° C. with constant agitation. After centrifugation of bacterial cells at 6,000 rpm for 10 min at room temperature, 100 ml of culture supernatant was mixed with 20 ml of Solution I (20% PEG 8000+2.5M NaCl) and incubated for 10 min at room temperature. The sample was then loaded in a column well containing borosilicate filters by applying vacuum for 10 min. The column was applied with 50 ml of Solution II (4M NaClO4, 50 mM Tris-HCl, pH 8.5) for both M13 lysis and binding, and incubated at room temperature for 10 min for complete lysis of bacteriophages. Vacuum was applied for 10 min to allow adsorption of LC-sense molecules to the filter. The column was then added with 100 ml of Solution III (80% EtOH, 20 mM NaCl, 2 mM Tris-HCl, pH 7.5) and applied with vacuum for 10 min. Washing step with Solution III was repeated again and the buffer solution was removed by applying vacuum for additional 15 min. LC-sense molecules was eluted with 10 ml of sterile water. LC-sense molecules were run on a 1% agarose gel and photographed under UV light for their quality and quantification.

Example 8

Results

Example 8.1

Preparation of LC-Sense Array

Figure 1:
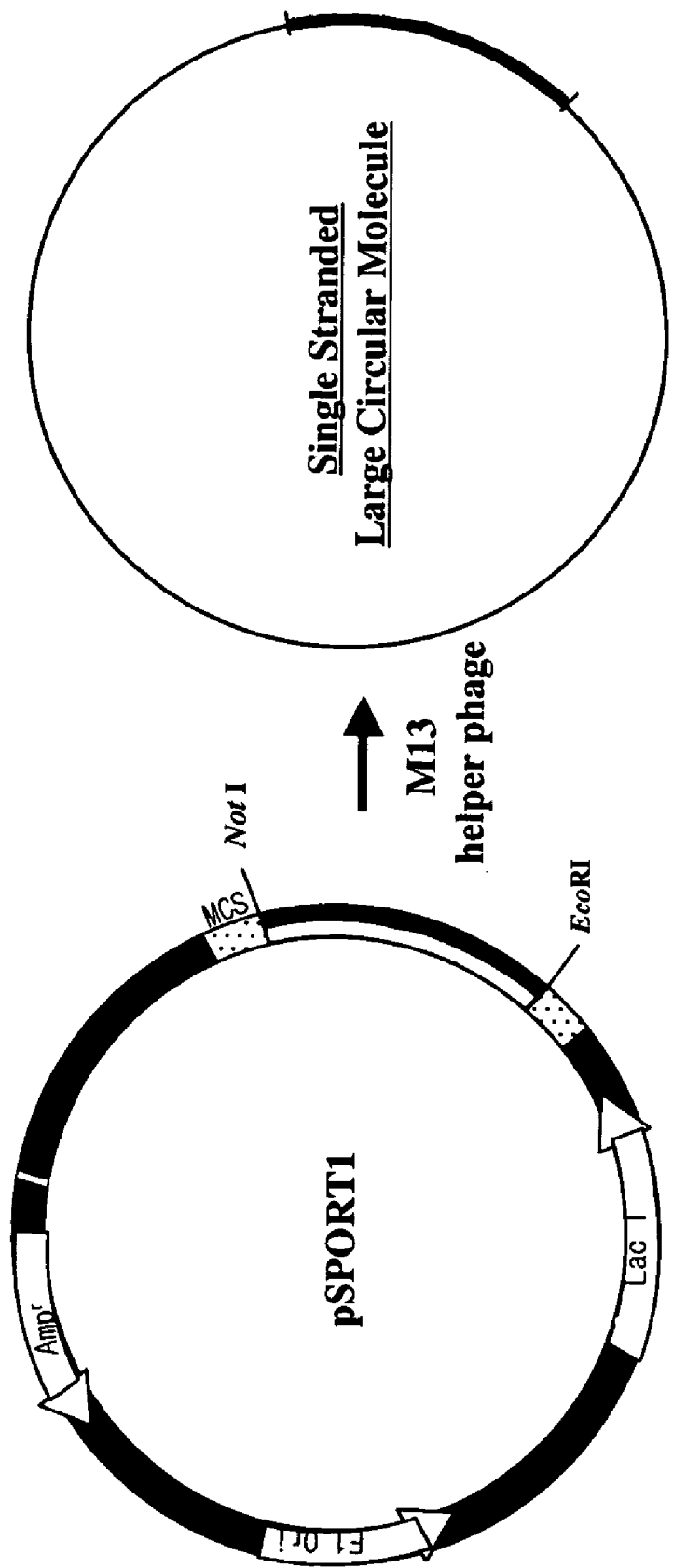
FIG. 1 shows a schematic diagram for production of single stranded LC-sense molecules. A cDNA of target gene is cloned into the multiple cloning site of a M13 phagemid vector. This construct allows the rescue of a single stranded LC-sense molecule of the target gene when infected with a helper phage, M13KO7.
Figure 2:
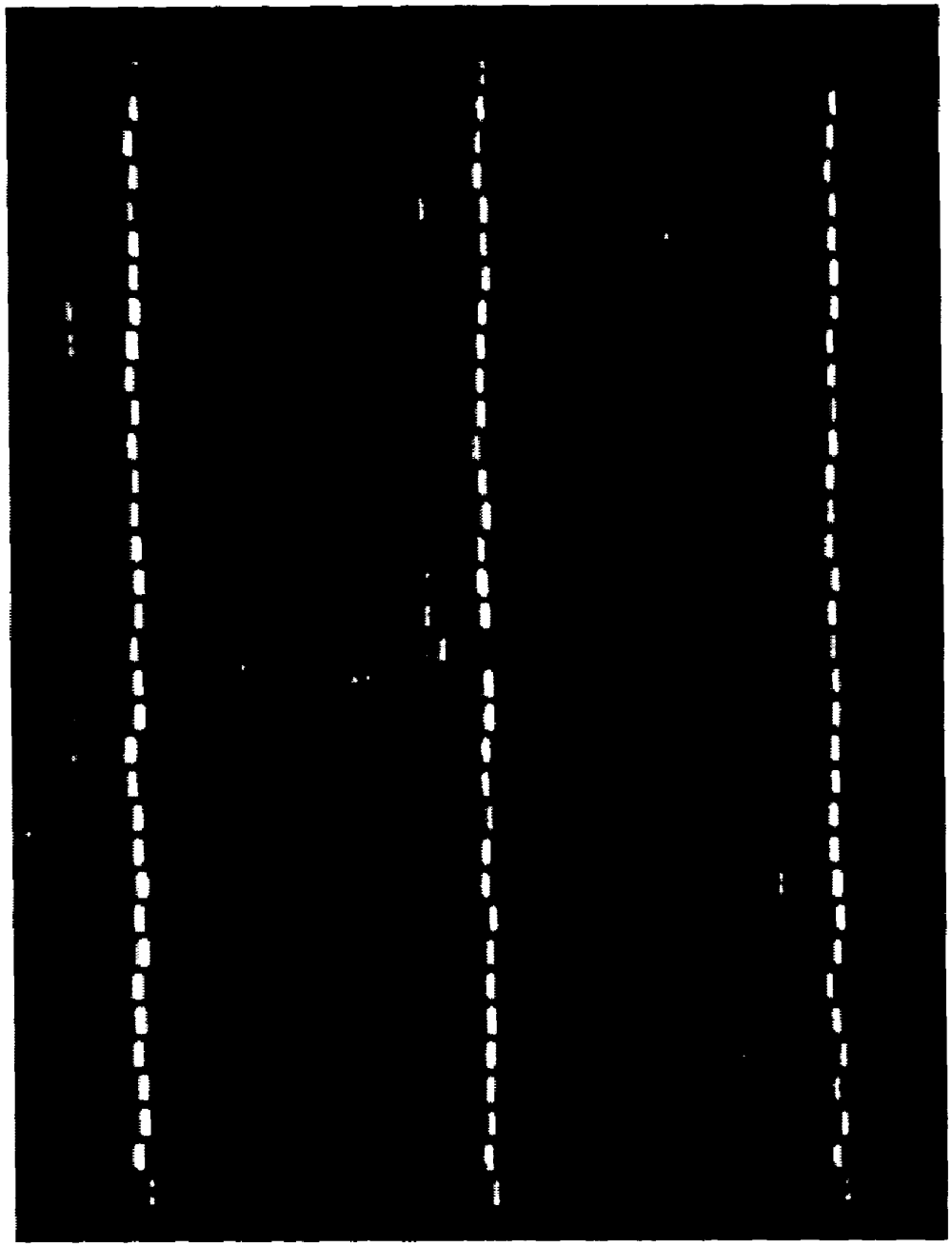
FIG. 2 shows large-scale production of LC-sense molecules in a small quantity. 1,152 transformants with recombinant pSPORT1 phagemid were incubated and infected with M13 helper bacteriophages in a 96-well format for high throughput massive production of LC-sense molecules.

We prepared a microarray with LC-sense molecules (FIG. 1) to examine their utility in massive profiling of differential gene expression. Competent E. coli cells containing a helper bacteriophage M13K07 was transformed with recombinant pSPORT1 phagemids of 1,152 nonredundant clones to produce LC-sense molecules. High throughput production of LC-sense molecules was performed in a 96-well format. The purified LC-sense molecules were electrophoresed on a 1% agarose gel and photographed under UV light (FIG. 2). The single stranded DNA samples of LC-sense molecules were arrayed on a silanized slide glass using a microarrayer.

Example 8.2

Melting Temperature of LC-Sense Molecules

The structural difference between single stranded LC-sense molecules and the double stranded phagemid DNA containing the TNF-α insert was also examined by measuring the melting temperature (Tm1/2). When absorbance at 260 nm was monitored for double-stranded phagemid DNA while temperature was raised progressively, a typical chromatic change was detected around 87° C. (FIG. 3A). However, when single stranded LC-sense molecules were examined for their melting temperature, the chromatic change of a mild slope was detected at around 54° C., indicating the denaturation of intra-molecular short duplexes (FIG. 3B). These results confirmed that the LC-sense molecules were single stranded molecules. Further, an optimal hybridization temperature was determined based on these results.

Example 8.3

Confirmation of RNA Quality

The quality of RNA often determines outcome of microarray experiments. Poly(A)$^+$ mRNAs prepared from normal and cancerous liver tissues were used to synthesize Cy3- dUTP or Cy5-dUTP-labelled cDNAs, respectively. The labeled cDNAs were mixed and allowed to hybridize to probe cDNA seeded on a DNA chip at 65° C. LC-sense microarray was washed and scanned by scanner (FIG. 4A), and analyzed by software. The data were then scatter-plotted after log2 transformation (FIG. 4B). Scanned images demonstrated that the quality of the RNA is pure enough to be of use for further labeling and hybridization to LC-sense array.

Example 8.4

Identification of Differentially Expressed Genes in Cancerous Liver Tissue

Poly(A)+ mRNA that was prepared and confirmed for its integrity as in EXAMPLE 8.3 was used to detect the expression profile of genes in cancerous liver tissue using the same procedures as described above except that labeled target cDNAs are loaded on a LC-sense microarray, and hybridization was performed at 60° C. LC-sense microarray was then scanned and analyzed for expression profile (FIG. 5). The data were then scatter-plotted after log2 transformation (FIG. 6). Genes with the sum of median value lower than 200 were excluded for further data processing. From the experiments, we discovered that 29 (~2.5%) of 1,152 genes were up-regulated in liver cancer tissue (Table 1). Among the 29 genes, in particular, CD44 antigen (Endo K. et al., *J. Hepatology*, 32(1):78-84, 2000), inosine monophosphate dehydrogenase (Jackson R. C. et al., *Nature* 256 (5515):331-333, 1975), multiple endocrine neoplasia 1 (Nakajima K. et. al. *Intern. Med.* 30(1):20-24, 2000), and calcium/calmodulin-dependent protein kinase 2 (Arizono K. et. al. *Life Sci.* 53(12):1031-1037, 1993) were previously reported as those involved in liver cancer progression. On the other hand, 6 of 1,152 genes were down-regulated in liver cancer tissue (Table 2). Among the 6 (~0.5%) genes, in particular, fibrinogen-like 1 (Kohno T. et. al., *Jpn. J. Cancer Res.* 91(11):1103-1110, 2000) was previously reported that its expression was down-regulated in adult T cell leukemia. These results indicate that LC-sense molecules can be used as binding agents for microarrays to detect genes with differential expression.

Example 8.5

Preparation of LC-Sense DNA in a Large Quantity

Production of LC-sense molecules on a large scale would be required for making a large number of DNA microarrays with consistent and dependable quality. Large scale production of LC-sense molecules has been accomplished with a semi-automatic "prototypical" instrument. The instrument is equipped with 96 purification columns with 37 mm inside diameter, two 8-well dispensers with 30 or 100 ml pumping capacity respectively and a vacuum manifold (60 W×42 L×60 H). A recombinant phagemid was transformed into competent *E. coli* cells containing a helper bacteriophage M13K07. A single colony was picked and seeded in 100 ml of LB liquid media, and cultured for 14 hrs at 37° C. with constant agitation. The LC-sense molecules were purified from 100 ml of the culture supernatant with the semi-automatic purification instrument. LC-sense molecules prepared on a large scale were run on a 1% agarose gel to test both their quality and quantity (FIG. 7). Out of 100 ml culture supernatant, approximately 200 μg of LC-sense molecules were obtained by using the instrument.

All of the references cited herein are incorporated by reference in their entirety.

Those skilled in the art will recognize, or be able to ascertain using no more than routine experimentation, many equivalents to the specific embodiments of the invention specifically described herein. Such equivalents are intended to be encompassed in the scope of the claims.

TABLE 1

List of up-regulated genes (>2X) in cancerous liver tissue.

| Gene Name | Accession NO. | Ratio of Median |
|---|---|---|
| CD44 antigen (homing function and Indian blood group system) | X66733 | 6.3 |
| Cytochrome P450, subfamily IIE (ethanol-inducible) | J02843 | 6.1 |
| Transcription elongation factor A (SII), 1 | | 5.8 |
| IMP (inosine monophosphate) dehydrogenase 2 | J04208 | 5.5 |
| ESTs, Weakly similar to KIAA0206 [*H. sapiens*] | AI193075 | 5.6 |
| Human skeletal muscle 1.3 kb mRNA for tropomyosin | A1797037 | 4.8 |
| KIAA0701 protein | AI797037 | 4.8 |
| MRNA for transcription elongation factor S-II, hS-II-T1 | NM_003195 | 5.2 |
| Deafness, autosomal dominant 5 | AF073308 | 5.1 |
| KIAA1037 protein | AI383628 | 4.8 |
| KIAA0375 gene product | AB002373 | 4.5 |
| Prefoldin 5 | AA287397 | 4.2 |
| KIAA0710 gene product | AB014610 | 4.1 |
| Paired-like homeodomain transcription factor 1 | U70370 | 4.3 |
| Retinal outer segment membrane protein 1 | L07894 | 4.4 |
| ESTs | Z39419 | 3.8 |
| MYC-associated zinc finger protein (purine-binding transcription factor) | M94046 | 3.6 |
| Ubiquitin-conjugating enzyme E2L 3 | AJ000519 | 4.1 |
| Novel human gene mapping to chromosome 1 | AL040438 | 3.9 |
| *Homo sapiens* clone 24421 mRNA sequence | AF070641 | 3.9 |
| *Homo sapiens* mRNA; cDNA DKFZp566J2146 | AL050081 | 3.5 |
| Chromosome condensation 1-like | NM_001268 | 3.5 |
| KIAA0902 protein | AB020709 | 2.9 |
| Multiple endocrine neoplasia I | Y12338 | 2.7 |
| Protein tyrosine kinase 9-like (A6-related protein) | AI188660 | 2.6 |
| ESTs, Weakly similar to ORF YOR150w [*S. cerevisiae*] | AI129433 | 2.4 |
| Transcription elongation factor B (SIII), polypeptide 2 | AW327285 | 2.4 |
| Calcium/calmodulin-dependent protein kinase kinase 2,beta | AI026833 | 2.4 |
| Cofactor required for Sp1 transcriptional activation, subunit 9 | AA665998 | 2.1 |

TABLE 2

List of down-regulated genes (>2X) in cancerous liver tissue.

| Gene Name | Accession NO. | Ratio of Median |
|---|---|---|
| Transmembrane protease, serine 2 | U75329 | 0.48 |
| Fibrinogen-like 1 | N92944 | 0.42 |
| Human gene isolated from PAC 272L16, chromosome 1, similar to calcium/calmodulin dependent protein kinases | AL023754 | 0.35 |
| CASP2 and RIPK1 domain containing adaptor with death domain | AA811130 | 0.35 |
| Ariadne homolog | AL040708 | 0.35 |
| NADH dehydrogenase (ubiquinone) flavoprotein 1 | AW250734 | 0.29 |

What is claimed is:

1. A method for making an array comprising a plurality of large circular-sense molecules bound to surface of a support, comprising (i) inserting a nucleic acid fragment into a vector that generates single stranded form of the vector;

(ii) preparing bacterial transformants by introducing the vector containing the insert into competent bacterial cells to make bacterial transformants;

(iii) infecting the transformants with helper phage to produce the large circular-sense molecule;

(iv) isolating the large circular-sense molecule from culture supernatant of the transformants; and (v) arraying the large circular-sense molecule onto the surface of a support.

2. The method of claim 1, wherein said large circular-sense molecule has a length of from about 1,000 to about 20,000 nucleotides.

3. The method of claim 2, wherein the length of the large circular-sense molecule has a length of about 1,000 to 8,000 nucleotides.

4. The method of claim 3, wherein the length of the large circular-sense molecule has a length of about 3,000 to 7,000 nucleotides.

5. The method of claim 1, wherein said support comprises a coating of amino-silane, poly-L-lysine or aldehyde.

6. The method of claim 1, wherein said support is slide glass, ceramic, inorganic-organic composite, flexible plastic film, silicon, metal, or membrane.

7. The method of claim 6, wherein the support is silanized glass slide.

8. The method of claim 1, wherein the nucleic acid fragment is inserted into the vector unidirectionally.

9. The method of claim 1, wherein the array is microarray.

* * * * *